United States Patent [19]

Fullemann

[11] Patent Number: 4,954,149
[45] Date of Patent: Sep. 4, 1990

[54] INJECTION SEPTUM

[75] Inventor: James S. Fullemann, Half Moon Bay, Calif.

[73] Assignee: Merlin Instrument Company, Half Moon Bay, Calif.

[21] Appl. No.: 427,033

[22] Filed: Oct. 25, 1989

[51] Int. Cl.⁵ .............................................. B01D 15/08
[52] U.S. Cl. .................................. 55/386; 210/198.2; 215/247; 215/310
[58] Field of Search .......................... 55/67, 197, 386; 73/23.1; 210/198.2, 198.3; 215/247, 292, 307, 310

[56] References Cited

U.S. PATENT DOCUMENTS

| | | | |
|---|---|---|---|
| 811,811 | 2/1906 | Allison | 215/247 |
| 2,579,724 | 12/1951 | Breakstone | 215/247 |
| 3,623,843 | 11/1971 | Brownlee | 55/386 X |
| 3,650,093 | 3/1972 | Rosenberg | 55/159 |
| 4,066,183 | 1/1978 | Armstrong | 215/247 |
| 4,084,718 | 4/1978 | Wadsworth | 210/198.2 X |
| 4,123,236 | 10/1978 | Hirschfeld et al. | 55/197 |
| 4,134,512 | 1/1979 | Nugent | 215/247 |
| 4,193,402 | 3/1980 | Rumpler | 215/247 X |
| 4,422,860 | 12/1983 | Feinstein | 55/67 |
| 4,515,752 | 5/1985 | Miramanda | 215/307 X |

FOREIGN PATENT DOCUMENTS

| | | | |
|---|---|---|---|
| 3435854 | 4/1986 | Fed. Rep. of Germany | 210/198.2 |
| 60-095348 | 5/1985 | Japan | 55/67 |
| 62-083658 | 4/1987 | Japan | 55/67 |
| 62-083660 | 4/1987 | Japan | 55/67 |

OTHER PUBLICATIONS

"Hewlett-Packard 1988 Analytical Supplies Catalog and Chromatography Reference Guide", p. 35, the Cool on-Column Inlet.

Primary Examiner—Robert Spitzer
Attorney, Agent, or Firm—Clifton L. Anderson

[57] ABSTRACT

A septum for an injection port of a gas chromatograph includes interlocked syringe and duckbill seals. The syringe seal prevents fluid leakage during injection by syringe. The duckbill seal prevents fluid leakage after the syringe needle is withdrawn from the septum. A spring clip is used to urge the duckbill closed as the needle is withdrawn. An advantage of this two component septum is that the duckbill slit can be precisely formed in the duckbill seal before the seals are engaged.

10 Claims, 6 Drawing Sheets

INJECTION SEPTUM

BACKGROUND OF THE INVENTION

The present invention relates to chromatography systems used for chemical analysis and, more particularly, to an improved septum for an injection port of a gas chromatography system.

In gas chromatography, samples are separated into their components by passing the sample through a separating column. The sample is introduced into a flowing carrier gas in the inlet system. The carrier gas sweeps the sample from the inlet system onto the separating column. The separated components emerging from the column are eluted through a detector which monitors the elution over time. A chromatogram, representing eluting quantity as a function of time, is generated by plotting the detector output signal.

Typically, the carrier gas is sealed from the outside world by a rubber septum which can be cut from a sheet of rubber approximately ⅛ inch thick. The sample is introduced into the inlet system through the septum using a syringe. The sample is drawn into the syringe, then the syringe needle is used to pierce the septum; the sample is injected into the inlet system and the syringe needle is withdrawn.

The septum must serve two functions. First, it must form a seal around the needle to prevent leaks while the injection is effected. Second, it must reseal the injection port after the syringe needle has been withdrawn and maintain this seal while the chromatographic separation is being executed. A leak occurring while the needle is in the septum can cause part of the injected sample to escape the injection system. This "injection" leak is difficult to detect because it occurs during the dynamic process of injection and is only apparent by careful examination of the quantitative results of the chromatogram. A failure to seal after the needle is withdrawn is more easily detected. The resulting "post-injection" leak is evident from variations in the characteristic retention time for a chromatographic peak resulting from variations in the column flow rate. Some capillary column injection ports may show different behavior for a post-injection leak because of their flow configuration.

Septum deterioration and resulting failure are serious problems. Monitoring a system for leaks can be costly and time consuming. Replacement of seals is inconvenient. Problems of detection and replacement are aggravated in automated systems which may run unattended for as many as 100 samples. A failure early in a run can impair the validity of the results for all subsequent samples.

Septum deterioration is inevitable due to the action of the syringe needles used for injection. Syringe needles must be strong enough to pierce the septa of sample containers and injection ports without bending or buckling. This strength requirement leads to the use of larger diameter needles. Larger diameter needles require greater insertion force to pierce a septum, which is thus subject to greater wear. The larger needles also make larger holes or tears in the septum, which are harder to reseal after needle withdrawal. Needles of smaller diameter cause less damage to the septum and make resealing easier, but are much more susceptible to bending when piercing a seal.

Syringe needles are made with sharp, beveled points to slice through the septa with lower force. However, the slicing action of repeated injections with beveled needles can macerate a septum, which then begins to leak. In addition, small pieces of rubber torn from a septum by the needles can fall into the injection port liner. Once in the liner, these pieces can affect the analysis in two ways. First, they can release compounds which can appear as "ghost peaks" in the chromatogram. Second, they can adsorb or partition sample components as they pass through the injection port, causing distortion of peak shapes in the chromatogram. In either case, the validity of the resulting chromatogram is impaired.

Taking into account these considerations, most gas chromatographs use a rubber septum, approximately 3 mm thick and 6-12 mm in diameter. Syringes typically used with such septa are 10 microliter total capacity, with a sharp beveled 26 gauge, i.e., 0.48 mm diameter, needle. These are used for both manual injection and for automatic liquid samplers. Alternatively, thicker "cylindrical" septa are used to improve the reliability of sealing after multiple injections. These have the disadvantage of requiring higher syringe force.

Especially strenuous demands are made on a septum in automatic liquid samplers, such as the Hewlett-Packard 7673A. This sampler uses a very rapid injection cycle. A differently shaped needle is adapted so that it can pierce a septum so that liquid sample can be injected into the injection port liner. The needle can be removed from the port in less than 0.25 seconds before the syringe needle contents can be heated significantly by the injection port or the septum. The needle has a relatively large diameter, e.g., 0.66 mm, to allow it to withstand the higher force required to pierce the septum at high speed without bending or buckling. The needle has a blunt tip which facilitates a properly directed spray pattern for the sample. The larger diameter and blunt tip cause greater damage to the septum per injection, thus shortening the septum life before leaks occur or pieces of septum fall into the injection liner.

The problem of maceration can be addressed by using a septum having a predefined path for needle penetration. For example, septa have been adapted from "duckbill" seals. A duckbill seal comprises a flat rubber tube with two flat surfaces which can seal against each other. Duckbill seals are often used as check valves in flow systems because they open with very low pressure drop in one direction while sealing in the other direction. Duckbill seals are effective under high pressure, which causes the flat surfaces to press against each other more tightly.

Because a slit is preformed between the flat surfaces, a blunt needle can be inserted with low force through a duckbill seal many times without tearing or crumbling the rubber by forcing the flat surfaces apart. However, the flat seals do not form an effective seal about a syringe needle so leaks can occur during injection. In addition, the low pressure drops across the seal can be insufficient to close the flat surfaces, allowing post-injection leaks. The problem with post-injection leaks can be remedied by adding a spring to force the sealing surfaces together. Another disadvantage of duckbill seals is that they have a long aspect ratio and do not fit into a conventional septum holder and therefore require a specially designed seal holder.

A duckbill seal has been included in an inlet assembly for a capillary column. For example, in the "Hewlett-Packard 1988 Analytical Supplies Catalog and Chromatography Reference Guide", page 35, a Cool On- Column Inlet is described including a duck bill. Inspection of the actual system reveals that a stainless steel probe is used to separate the duckbill surfaces. Once the surfaces are separated by the probe, the needle is extended through the probe and the probe is withdrawn so that the duckbill closes around the needle. Neither the probe nor the duckbill seals the needle completely, so that some leakage generally occurs. It is noted that the inner perimeter of the duckbill seal is about 1.6 mm at the duckbill end and about 3.1 mm at the end where the needle is first inserted, so that this latter end never forms a seal with the needle.

The foregoing are but a few of the wide variety of commercially available septa. Other examples are described in catalogues from gas chromatography suppliers. The wide variety of septa available with differing claims for pierceability, temperature stability, and number of injections show that there is a need for a more durable septum. In addition, the availability of needle guides and a needle guide with a "backup" seal in case the septum fails is further evidence that there is a need for an improved and more reliable septum. Preferably, such a septum would accommodate conventional form factors rather than requiring a specially designed seal holder.

SUMMARY OF THE INVENTION

In accordance with the present invention, a septum for use in gas chromatography is fabricated from flexible material and defines an aperture which is annular at an insertion end and duckbill-shaped at an injection end. This structure can be conveniently manufactured by assembling two components, each bearing a respective form of the aperture. A spring can be included to urge the duckbill end of the aperture to close when no needle is extending therethrough. The inner perimeter of the annular end of the aperture is slightly smaller than the circumference of the syringe needle so that the aperture expands slightly to form a seal when the needle is inserted. The inner perimeter of the duckbill end of the aperture is larger than the circumference of the syringe needle to permit the needle to pass through easily. Both aperture ends conform to the same needle diameter.

As indicated above, a septum must perform two functions, i.e., sealing during injection and sealing after injection. In the septum of the present invention, each aperture end performs a respective one of these functions. The cylindrical end seals against a syringe needle during injection, while the duckbill seals the inlet system as the needle is withdrawn. At no time is there fluid communication between the inlet system and the external environment. Since the present invention provides an aperture for a blunt syringe needle, shredding is minimized. The seal is well-suited for both manual and automated insertion. The seal has the same form factor as a conventional septum to allow convenient replacement. These and other features and advantages of the present invention are apparent from the description below with reference to the following drawings.

DESCRIPTION OF THE PREFERRED EMBODIMENTS

Figure 1A:
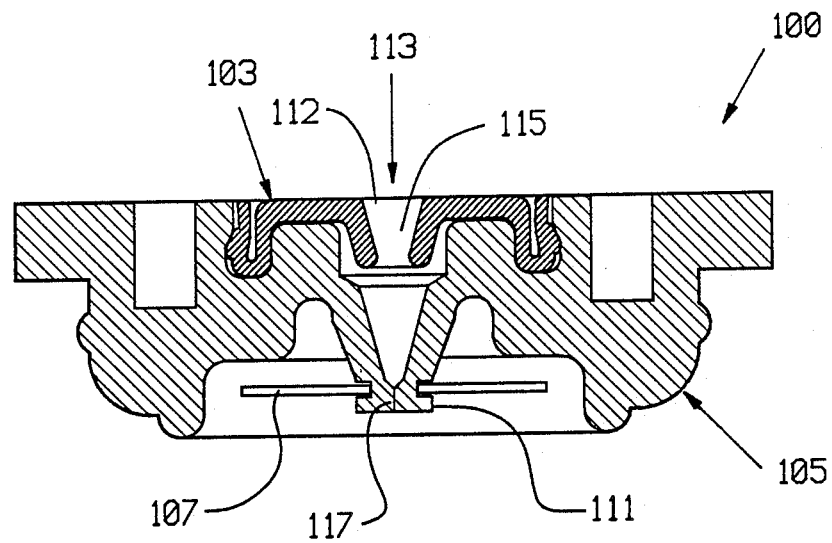
FIGS. 1A and 1B are sectional views of a septum without and with, respectively, a syringe needle extending therethrough in accordance with the present invention. The section of FIG. 1B is orthogonal to the section of FIG. 1A.
Figure 1B:
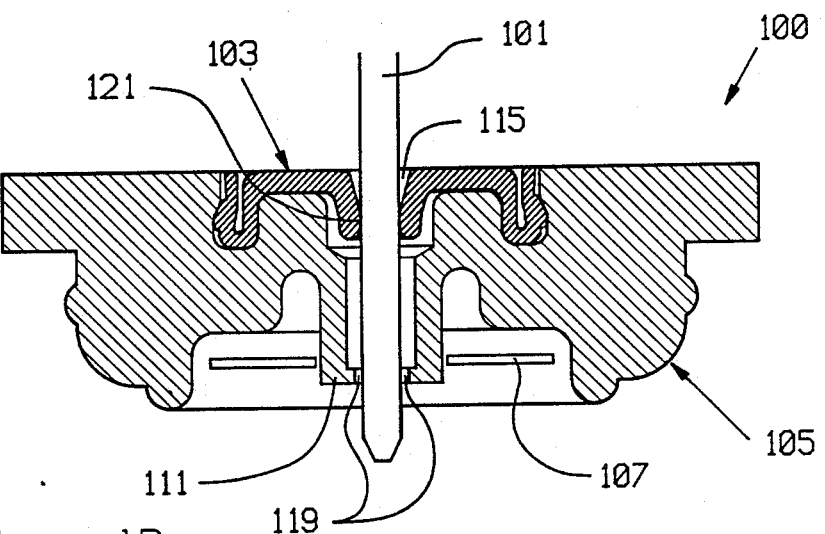

In accordance with the present invention, a septum 100 provides for effective sealing both in the absence of a syringe needle, as shown in FIG. 1A and with a syringe needle 101 extending therethrough, as shown in FIG. 1B. Septum 100 includes three parts which snap together: a syringe seal 103, a duckbill seal 105, and a spring clip 107. Syringe seal 103 is seated in and interlocked with duckbill seal 105 so as to define a complex septum aperture 113 which is annular at its upper end 112 and flat at its lower duckbill end 111 in the absence of a syringe needle extending therethrough. Septum aperture 113 includes an annular aperture 115 formed in syringe seal 103 and a duckbill aperture 117 formed in duckbill seal 105. Syringe seal 103 provides a sliding seal around an injecting needle 101 while duckbill seal 105 seals in the absence of such a needle. Clip 107 forces duckbill end 111 closed before a needle is completely withdrawn from annular aperture 115. Thus, septum 100 allows injection while preventing unintended leakage. Illustrated septum 100 has an overall geometry which allows it to be used as a replacement for a conventional septum.

Figure 2A:
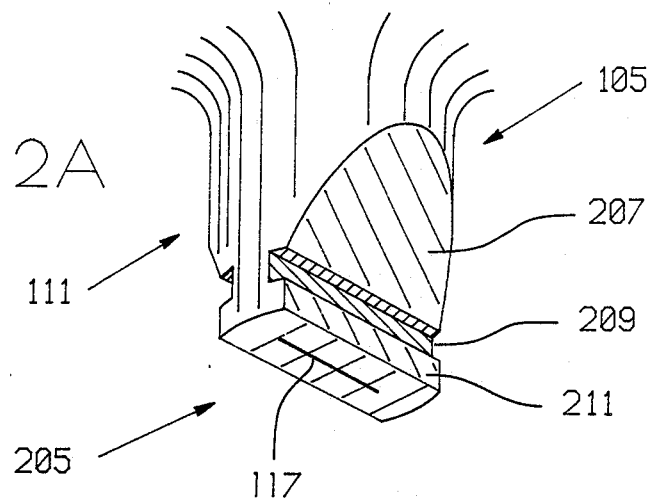
FIGS. 2A and 2B are perspective views of the duckbill end of the septum of FIGS. 1A and 1B without and with, respectively, a syringe needle extending therethrough.
Figure 2B:
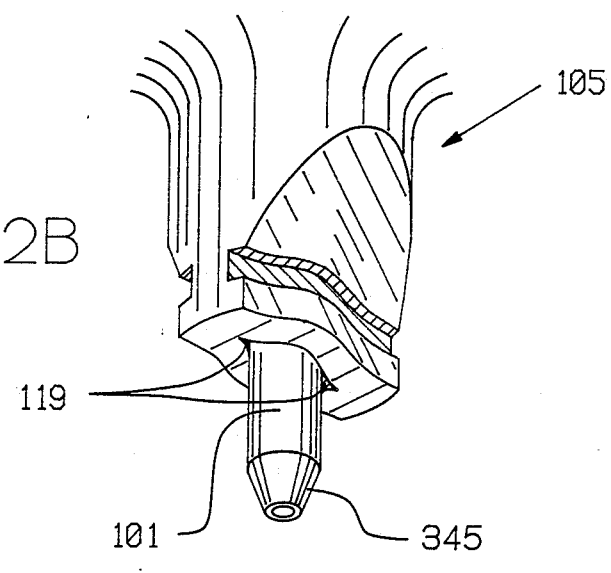

The complementary function of seals 103 and 105 in septum 100 is illustrated schematically by comparing FIG. 1B with FIG. 1A, and comparing FIG. 2B with FIG. 2A. FIGS. 1A and 2A show duckbill 117 aperture in the absence of a needle. In practice, especially under the force of clip 107, duckbill aperture effectively prevents fluid leakage. However, when needle 101 extends through septum 100, duckbill seal 105 does not seal against needle 101 reliably, as indicated in FIG. 2B. In particular, leakage can occur near the extremes 119 of duckbill end 111. However, syringe seal 103 does effectively seal against needle 101 when the latter extends through septum 100, as indicated in FIG. 1B. Conversely, syringe seal 103 is not necessarily leakproof in the absence of a needle, as indicated in FIG. 1A; however, it need not be since duckbill seal 105 prevents leaks in this condition. Thus, leaks are prevented by duckbill seal 105 in the absence of a needle and by syringe seal 103 in the presence of needle 101.

Figure 3:
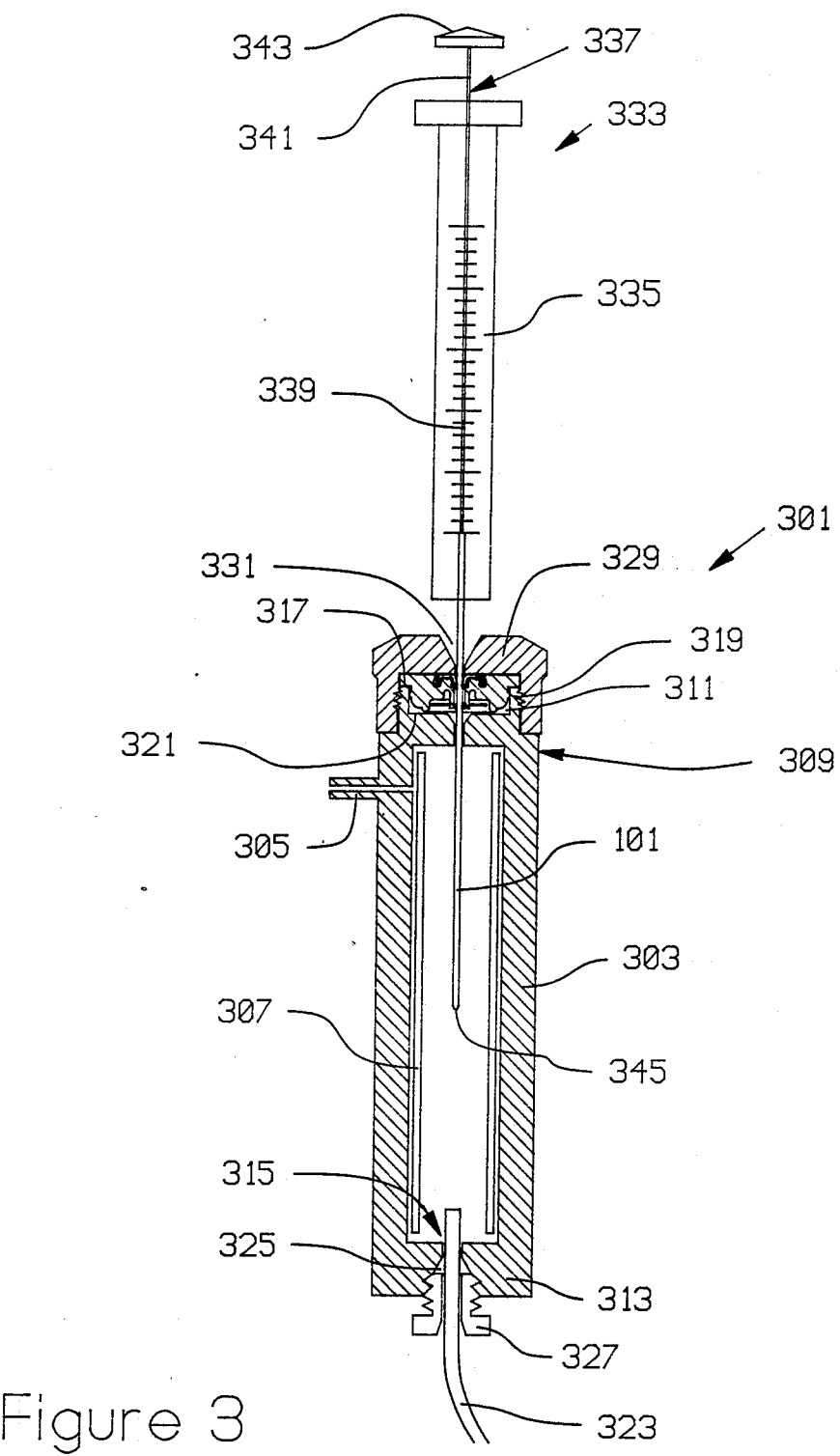
FIG. 3 is a sectional view of an inlet injection port incorporating the septum of FIG. 1A during a step in which fluid is introduced into the port by a syringe.

Septum 100 is designed to be used in an injection port 301, shown in FIG. 3. Injection port 301 has a body 303, a carrier gas inlet 305, a liner 307, a top 309 with a sample inlet 311 and a bottom 313 with an outlet 315. Top 309 includes a reference plane 317 and a threaded annular ridge 319 defining a septum cup 321. Outlet 315 widens toward the exterior of body 303 to facilitate insertion and sealing of a separation column 323. Sealing is effected using a conical seal 325 secured by a column nut 327. Sample inlet 311 widens toward the exterior of body 303 to facilitate sample insertion. A septum nut 329 has an aperture 331 which is similarly beveled for the same purpose. The female-threaded septum nut 329 secures septum 100 within septum cup 321, as shown in FIG. 3. As those skilled in the art can recognize, the foregoing can be extended to apply to injection ports with different flow configurations for packed and capillary columns.

A primary objective of the present invention is to provide reliable sample injection into port 301 using a syringe 333, which includes a graduated cylinder 335, syringe needle 101, and a plunger 337, as shown in FIG. 3. Plunger 337 includes a piston 339, a shaft 341 and a plunger cap 343. Syringe 333 is a conventional 10 microliter syringe. The tip 345 of needle 101 is relatively blunt so as to minimize piercing or slicing of septum 100.

Figure 4:
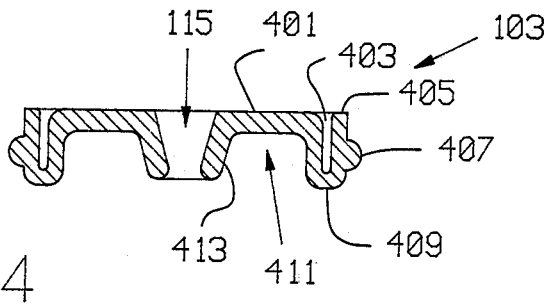
FIG. 4 is a sectional view of a syringe seal of the septum of FIG. 1A.

Syringe seal 103 is designed to provide a sliding seal around syringe needle 101 during the injection process. Syringe seal 103 has axial symmetry and includes central annular aperture 115, an inner ledge 401, a narrow upper groove 403, an upper rim 405, a circular rib 407, a lower rim 409, a wide lower groove 411, and annular web 413, as shown in FIG. 4. Annular aperture 115 is tapered so that it is relatively wide at its upper end to help guide needle insertion and relatively narrow toward its lower end to provide a tight seal about an inserted needle. Annular web 413 and wide lower groove 411 permit annular aperture 115 to accommodate needle misalignment.

Syringe seal 103 is formed of elastic material; preferably, syringe seal 103 and duckbill seal 105 are of molded rubber. Annular aperture 115 is dimensioned to permit sealable insertion of needle 101. The unstretched minimum inside diameter of annular aperture 115 is selected to accommodate needles having outer diameters which are from 0% to 40%, and preferably about 20%, larger. Some stretching of syringe seal 103 is desired to provide a snug seal against needle 101 formed by needle-to-syringe seal contact 121.

Rib 407 is used for interlocking seals 103 and 105 when the former is inserted into the latter using a tubular insertion tool. Narrow upper groove 403 receives the tubular insertion tool for septum assembly. In addition, grooves 403 and 411 define a spring which permits rib 407 to contract radially as syringe seal 103 is snapped into position in duckbill seal 105. When the insertion tool is removed, rim 405 expands radially under pressure to effect interlocking of seals 103 and 105, as shown in FIG. 1A.

Figure 5:
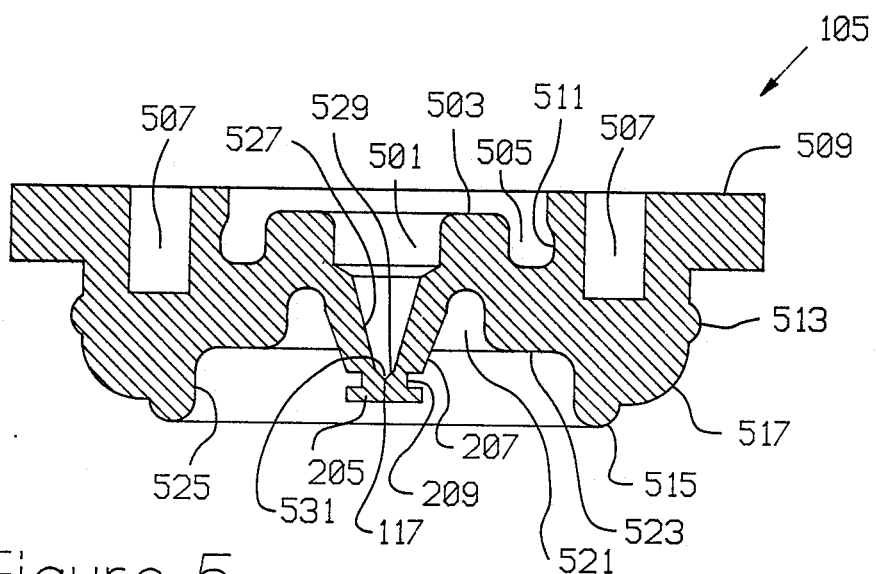
FIG. 5 is a sectional view of a duckbill seal of the septum of FIG. 1A taken along the same line as FIG. 1A.

Duckbill seal 105 is designed to provide a pressure seal for injection port 301 when syringe needle 101 is not inserted. Duckbill seal 105 includes, from top center and radially outward, an upper annular cavity 501, an upper annular ridge 503, an upper annular groove 505, alignment holes 507, and a flange 509, as shown in FIG. 5. These features are dimensioned to receive syringe seal 103, as shown in FIG. 1A. Specifically, upper annular seat 501, which opens into duckbill aperture 117, is large enough to admit syringe seal web 413 and allow it lateral movement to accommodate needle misalignment. Upper annular ridge 503 of duckbill seal 105 mates with wide lower groove 411 of syringe seal 103 and upper annular grove 505 of duckbill seal 105 mates with lower rim 409 of syringe seal 103. In addition, upper annular groove 505 includes a lateral groove 511 which mates with rib 407 of syringe seal 103.

Flange 509, which seals against injection port ridge 319, is secured between septum nut 329 and injection port top 309 when septum 100 is installed in injection port 301, as shown in FIG. 3. Septum nut 329 is designed to stop itself at reference plane 317 to impose a predetermined amount of compression of flange 509 between septum nut 329 and ridge 319. Upon compression, flange 509 should be between 97% and 50%, and preferably about 80%, of its thickness in the absence of compression. The resulting deformation of flange 509 forces it into intimate contact with ridge 319 and nut 329 so as to produce a very reliable seal even in the presence of irregularities and small defects in the surfaces contacted. Duckbill seal 105 also includes lateral and downward circular ribs 513 and 515, separated by an outer wall 517 of arcuate cross section, to improve the seal against cup 321 because they can be deformed with relatively little force due to their small contact area. Lateral rib 513 also facilitates centering of septum 100 in cup 321.

Duckbill seal 105 further includes, from lower center and radially outward, lips 205, a lower annular groove 521, and a seat 523 and an associated sidewall 525 to accommodate clip 107. Lips 205 define a web which, like web 413, accommodates needle misalignment. As best shown in FIG. 2A, the outer surface 207 of lips 205 is tapered at an angle of approximately 75°. Duckbill end 111 terminates with a lateral groove 209 for engaging clip 107 and rim 211 preventing escape of clip 107. The inner surface 527 of duckbill end 111 is tapered to define a wedge shape terminating in a more blunt tapered groove 529 with an angle of about 90°, as shown in FIG. 5.

An advantage of the snap together design of suptum 100 is that duckbill aperture 117 can be formed from the inside, facilitating its alignment with the bottom of groove 529. Proper alignment of duckbill aperture 117 with the elongated apex 531 of groove 529 permits the latter to guide needle 101 into the former as needle 101 penetrates septum 100. Alignment holes 507, shown in FIG. 5, provide for placement of duckbill seal 105 on an alignment fixture in the slitting process.

Duckbill end 111 of duckbill seal 105 prevents fluid leakage of pressurized gas in injection port 301 through the center of septum 100. Fluid pressure in lower groove 521 tends to force septum 100 to expand against ridge 319 providing an addition seal against fluid leaks. Circumferential rib 513 helps to center septum 100 in cup 321 by providing contact between duckbill seal 105 and ridge 319, even if the inside diameter of cup 321 varies by as much as the thickness of rib 513.

Seals 103 and 105 can be molded from rubber. The rubber can be silicone, chlorofluorocarbon, urethane, or any other type of moldable rubber compound which has the desired physical and chemical properties. Septum 100 is about 11 mm in diameter and about 3 mm thick. Other dimensions can be accommodated.

Clip 107 is designed as a spring closure for duckbill seal 105 to provide rapid closure as syringe needle 101 is removed and to provide for reliable sealing even with low injection port pressure. The overall geometry of clip 107 is circular and flat to allow it to fit in seal 107 without touching or binding except at groove 209 of duckbill end 117.

Figure 6:
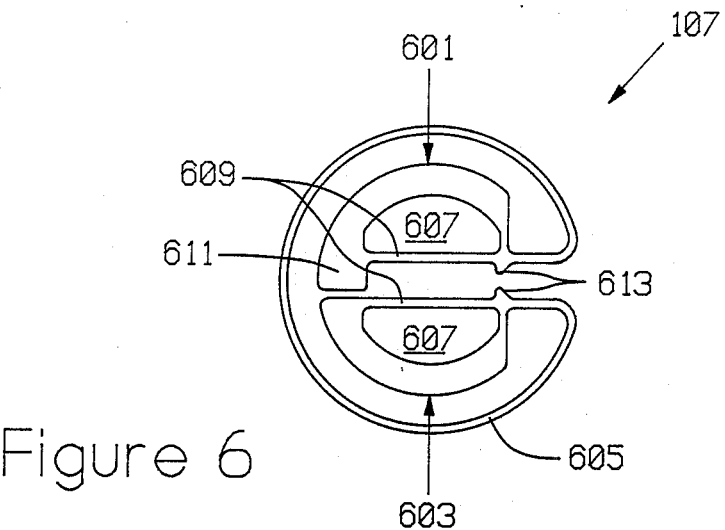
FIG. 6 is a plan view of the spring clip of the septum of FIG. 1A.

Clip 107 includes a pair of opposing pincer halves 601 and 603 which are flexibly connected by an arcuate ring 605, as shown in FIG. 6. Pincer halves 601 and 603 remain parallel as they are forced apart during insertion of needle 101 into duckbill seal 105. Apertures 607 are formed in each pincer half to receive an insertion tool, such as snap-ring pliers. The insertion tool forces pincer halves 601 and 603 apart during placement of clip 107 into seat 523 while allowing pincer edges 609 to clear duckbill rim 211. Pincer halves 601 and 603 are allowed to spring back together, allowing pincer edges 609 to rest in lateral grooves 209. Once clip 107 is received, the tool is removed. Protrusions 611 and 613 the prevent clip 107 from slipping out of groove 209. With clip 107 mounted in groove 209, spring tension in ring 605 forces pincer halves 601 and 603 toward each other, urging duckbill aperture 117 to close when no needle is inserted therethrough.

During the injection process, syringe needle 101 is inserted through septum aperture 113. Annular aperture 115 expands, preferably about 20%, as needle 101 penetrates and forms a sliding seal around needle 101. As needle 101 penetrates duckbill end 111, it forces its way through aperture 117, opening the duckbill. Fluid pressure in inner annular region 301 forces annular web 413 more tightly into syringe seal contact 121, improving the effectiveness of syringe seal 103. After full penetration of septum 100 by needle 101, the sample can be expelled from needle 101 and injected into injection port 301.

Once sample injection is complete, needle 101 is withdrawn. Spring clip 107 forces lips 205 of duckbill seal 105 to close quickly and reliably. Once duckbill 105 is closed, the fluid pressure of the carrier gas forces lips 205 together, ensuring a good seal at high or low pressures. The duckbill seal is effected before the sliding seal around needle 101 is broken by complete removal.

Note that each seal 103 and 105 is designed to accommodate needle misalignment. In effect, annular aperture 115 and duckbill aperture 117 are suspended on webs of rubber, e.g., web 413 and duckbill end 111, permitting them to move laterally or to change angle as needed to conform to needle 101. This floating characteristic helps prevent leakage that might be caused when needle 101 presses unevenly on syringe seal aperture 115.

Figure 7:
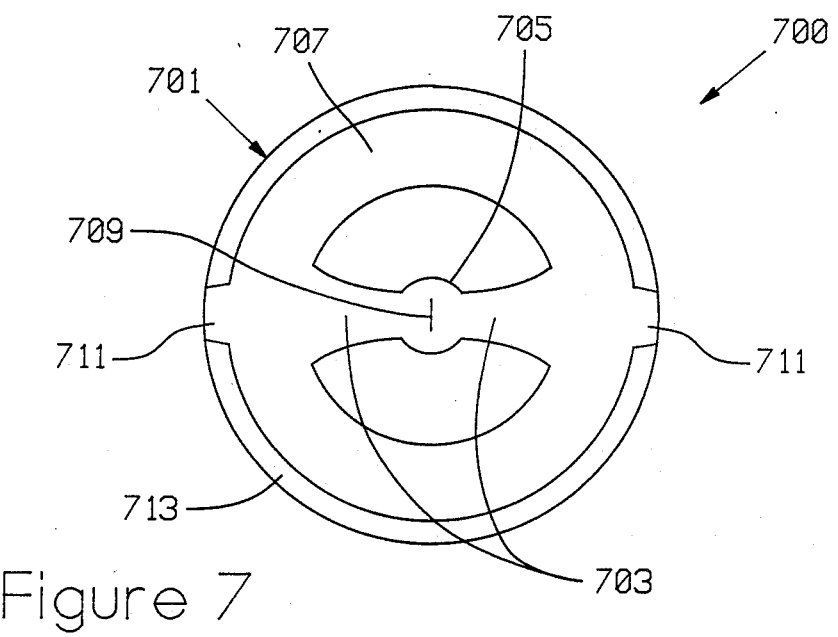
FIG. 7 is a bottom view of an alternative septum in accordance with the present invention.

An alternative septum 700 in accordance with the present invention uses a duckbill seal 701, shown in FIG. 7, with radial ribs 703, molded into duckbill seal 701 between center region 705 and outer rim 707, which urge a duckbill aperture 709 to close as a needle is withdrawn. At the radial extremes of radial ribs 703 are vertical ribs 711. These vertical ribs 711 extend up the outside of outer rim 707 and can intersect circular ribs 713, similar to circular ribs 513 and 515 of septum 100. Vertical ribs 711 are compressed radially when septum 700 is inserted into a septum cup. The compression force is transferred radially along radial ribs 703 toward duckbill aperture 709, forcing it closed. This restoring force serves the same function for septum 700 as clip 107 does for septum 100. This alternative septum 700 employs a syringe seal such as syringe seal 103. The syringe seal and duckbill seal 701 interlock in the same manner as seals 103 and 105. When so interlocked the seals of the alternative embodiment define a septum in accordance with the present invention.

Figure 8:
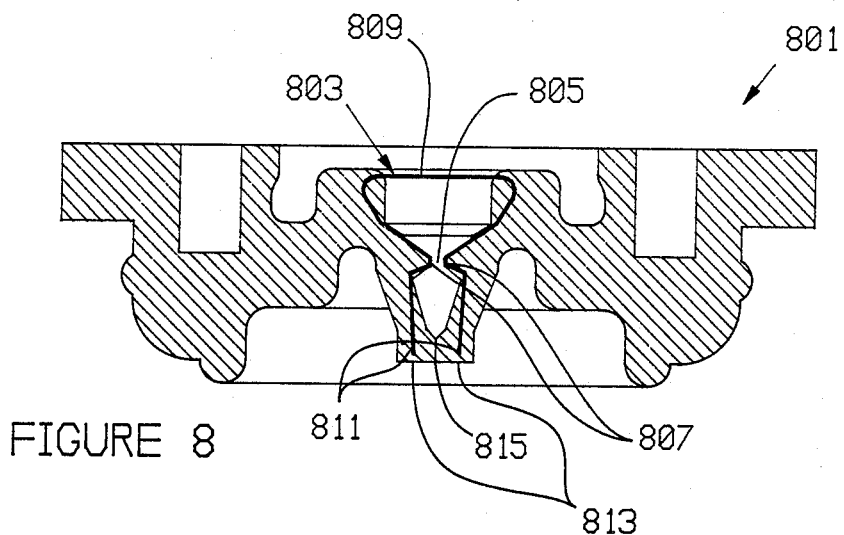
FIG. 8 is a sectional view of an alternative duckbill seal incorporating a spring clip molded in place.
Figure 9:
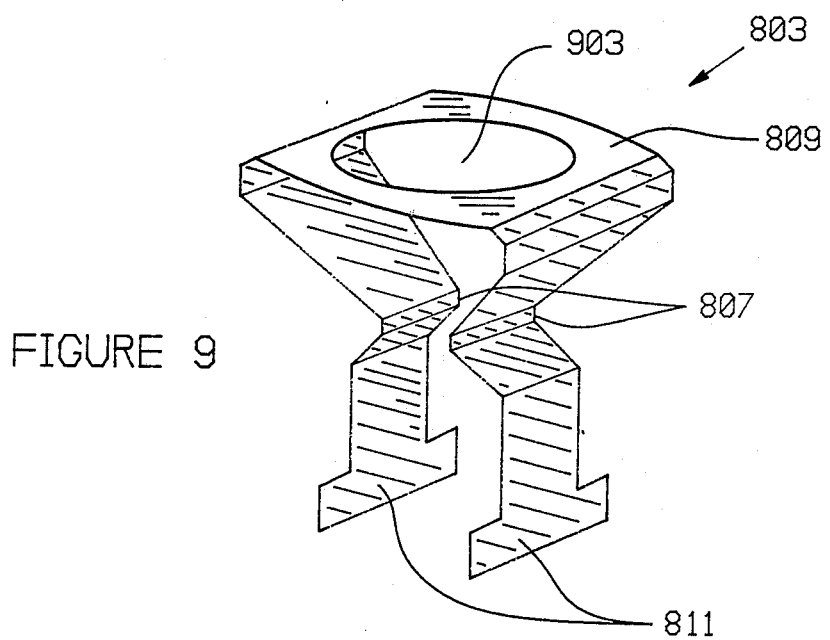
FIG. 9 is a perspective view of the spring clip of FIG. 8.

An alternative embodiment of the present invention incorporates a duckbill seal 801 having a curved spring clip 803 molded therein, as shown in FIG. 8. Molded clip 803 serves essentially the same purpose as spring 107 of duckbill seal 105. A gap 805 between spring protrusions 807 is spread when spring clip 803 is placed in a mold to create tension at an upper end 809 of spring clip 803. Spring ends 811 are molded inside duckbill lips 813. After rubber is molded around spring clip 803 to form duckbill seal 801 and after seal 801 is removed from the mold cavity, the force due to the spring tension in upper end 809 urges protrusions 807 and spring ends 811 together, urging duckbill aperture 815 closed. Spring clip 803 includes a hole 903, shown in FIG. 9, to accommodate passage of a syringe needle therethrough.

Flangeless versions of the septa described above can be fabricated which rely on one or more outer circular ribs to seal against a septum cup. These ribs have outside diameters larger than the inside diameter of the receiving cup, providing an interference fit when the septum is in place. As with septum 100, pressure in a lower groove of the duckbill seal forces these ribs into better contact with the septum cup, improving the reliability of the seal at higher pressures.

The present invention can be used in other applications where septa are employed. For example, a septum in accordance with the present invention can be used on a sample vial whose contents are sampled with a syringe. Also, such a septum can be used for pressurized sample containers, such as for natural gas samples. Such septa can be used as interlocks of sample or measurement probes inserted into pressurized vessels such as reactors. In general, septa in accordance with the present invention can be used for inserting samples into pressurized regions without leaks due to insertion.

In addition to the embodiments described above, the present invention provides for a monolithic septum with annular and duckbill ends of a unitary aperture. Such a septum differs from conventional and other known duckbill seals in that, when a needle is extended through the septum, the annular aperture and the duckbill aperture expand elastically to accommodate the needle and press against the needle under the pressure of their deformation. A wide variety of elastically deformable materials can be employed in the septum provided by the present invention. In addition, interlocking of components of a compound septum can be effected using a variety of means. Dimensions can be changed to accommodate devices and applications other than those illustrated.

The duckbill seal can be slit from the top or from the bottom. Alternatively, the slit can be molded in when the duckbill is molded. Also, the slit can be partially formed and a membrane can be torn by a tool or by the syringe upon first injection. These and other modifications to and variations upon the described embodiments are provided for by the present invention, the scope of which is limited only by the following claims.

What is claimed is:

1. A septum for permitting injection of a fluid by extension of a needle therethrough, said needle having an injection diameter, said septum comprising:
aperture means for defining a complex aperture, said complex aperture including an annular aperture with a minimum diameter and a duckbill aperture with a duckbill perimeter, said aperture means including elastic material bounding said complex aperture, said minimum diameter being less than said injection diameter when no needle is penetrating therethrough, said minimum diameter being substantially equal to said injection diameter when said needle penetrates said annular aperture, said perimeter being at least as great as said injection diameter when said needle penetrates through said duckbill aperture, said elastic material contacting and generally conforming to the cross section of said needle at said annular aperture and said duckbill aperture when said needle extends completely through said complex aperture.

2. The septum of claim 1 wherein said aperture means includes a syringe seal defining said annular aperture and a duckbill seal defining said duckbill aperture, said seals being interlocked so that said annular aperture and said duckbill aperture are aligned to constitute said complex aperture.

3. The septum of claim 2 wherein said aperture means includes closure means for urging said duckbill seal closed as said needle is withdrawn from said aperture means.

4. The septum of claim 3 wherein said closure means includes ribbing integral with said duckbill seal.

5. The septum of claim 3 wherein said closure means includes a spring clip.

6. The septum of claim 5 wherein said spring clip is molded into said duckbill seal.

7. A method of manufacturing the septum of claim 2, said method comprising:
  forming said syringe seal and said duckbill seal of elastic material so that said syringe seal includes said annular aperture and so that said duckbill seal includes a central aperture terminating in a wedge-shaped groove having an elongated apex, said seals being formed to be interlocking upon engagement with said syringe seal being disposed on the side of said duckbill seal opposite said wedge-shaped groove;
  inserting a slitting tool through said central aperture so that it is aligned with said elongated apex;
  slitting said elastic material at said elongated apex to define a slit; and
  mating said syringe seal and said duckbill seal so that they are interlocked and so as to define said complex aperture.

8. The method of claim 7 further comprising a step of disposing a clip on said duckbill seal so as to urge said slit closed, said forming step being further characterized in that said duckbill seal is formed so as to be able to engage and retain said clip.

9. The method of claim 7 wherein said forming step involves forming radial ribs on said duckbill seal so as to urge slit closed.

10. The method of claim 7 wherein said forming step involves inserting a spring into the rubber mold so that said duckbill seal includes said spring which urges said slit closed.

* * * * *